United States Patent [19]

Kruegle et al.

[11] Patent Number: 5,777,715
[45] Date of Patent: Jul. 7, 1998

[54] LOW VISION REHABILITATION SYSTEM

[75] Inventors: Herman A. Kruegle; Allen Blumenthal, both of River Vale, N.J.

[73] Assignee: Allen Vision Systems, Inc., Haverford, Pa.

[21] Appl. No.: 786,200

[22] Filed: Jan. 21, 1997

[51] Int. Cl.$^6$ .................. G02C 1/00; G06K 9/40
[52] U.S. Cl. .................. 351/158; 351/41; 382/54
[58] Field of Search .................. 351/41, 158, 203, 351/205, 209, 210; 382/54; 348/62, 63

[56] References Cited

U.S. PATENT DOCUMENTS

| | | | |
|---|---|---|---|
| 4,704,000 | 11/1987 | Pekar et al. | 351/41 |
| 5,106,179 | 4/1992 | Kamaya et al. | 351/158 |
| 5,129,716 | 7/1992 | Holakovszky et al. | 351/158 |
| 5,151,722 | 9/1992 | Massof et al. | 351/158 |
| 5,642,221 | 6/1997 | Fischer et al. | 351/158 X |

*Primary Examiner*—Huy Mai
*Attorney, Agent, or Firm*—Austin R. Miller

[57] ABSTRACT

The present invention is a head-mounted vision rehabilitation system for aiding in the rehabilitation of the visually impaired which includes a headset having an anterior portion extending over a patient's eyes and a posterior portion partially encircling the patient's head; a camera for imaging an image source which includes a focusing means and an electro-optical sensor to create an image signal based upon light from the image source; a coherent video display located within the anterior portion of the headset for receiving the image signal and recreating the image onto the patient's eyes; a disengageable connector for removably attaching the camera to the anterior portion of the headset; and a control unit in communication with the camera, the video display and the headset for controlling the operation of the head-mounted vision rehabilitation system. The present invention further includes a scanning system for scanning the image source without movement of the headset and a stabilization system for stabilizing the image recreated from the video display.

12 Claims, 9 Drawing Sheets

LOW VISION REHABILITATION SYSTEM

FIELD OF THE INVENTION

The present invention relates to a vision enhancement system for aiding in the correction of the vision of the visually impaired, particularly to a head-mounted visual aid device for assisting the visually impaired, and more particularly to a lightweight, modular headset incorporating a plurality of interchangeable components which allows for the implementation of a number of vision rehabilitation features selected in accordance with the particular visual impairment to be improved.

BACKGROUND OF THE INVENTION

The majority of people in the world today suffer from some type of visual impairment. Normally, this impairment is minor and can be adequately compensated for by using corrective lenses in the form of glasses or contact lenses. However, many people are forced to cope with more severe forms of visual impairment that cannot adequately be corrected by these means.

Macular Degeneration, a form of low vision, is one such type of impairment. Low vision is generally considered to be vision poor enough to keep someone from being able to read the newspaper while wearing their regular glasses. Visual acuity that results in this type of impairment can range anywhere from 20/20 (with a very constricted visual field) to 20/400 or worse, depending on what is causing the poor vision. Low vision is caused by a variety of diseases or conditions. Macular Degeneration itself accounts for about 65% to 75% of patients requesting vision rehabilitation. Diabetic Retinopathy, Glaucoma, Hereditary retinal degenerations or diseases such as Retinitis Pigmentosa, Albinism, Lebers Optic Neuropathy, Bests Disease and other conditions such as strokes or brain tumors account for the remainder of low vision conditions.

In order to cope with this disease, individuals work closely with a Low Vision Rehabilitation Specialist (an optometrist or ophthalmologist who has a special interest in and who has been trained in Low Vision Rehabilitation) or other professionals who specialize in specific aspects of low vision rehabilitation, such as occupational therapists, orientation and mobility instructors, educators who specialize in teaching both children and adults with poor vision, social workers and researchers. Low Vision Rehabilitation is available in most major medical centers and, in some cases, in private practices.

A Low Vision evaluation begins with a comprehensive patient history. This includes a medical, drug, social, work, and vision history. A meticulous refraction is then done to determine the patient's best possible visual acuity. Additional tests are done to determine what is needed to enable the patient to read. This correction may range from a simple pair of reading glasses to a magnifier or a complex system such as a telemicroscope or CCTV (closed circuit TV).

Other areas of the patient's lifestyle are addressed such as work needs, hobbies, social needs, recreational needs, financial and personal needs. For example, complex systems can be designed for someone who works on a computer and who needs large print or voice-activated programs. Every effort is made to enable the individual to continue working at his/her present job, or, if necessary, retraining individuals in new areas of employment.

Low Vision Rehabilitation is an approach to making the best possible use of the healthy vision remaining in the eye. The Low Vision Specialist has at her/his disposal a vast array of devices designed to help the visually impaired see better. These can include magnifiers, microscopic lenses, telescopes, electronic devices such as closed-circuit TV's, even virtual imagery. Proper lighting used in the proper manner, bold lined writing utensils and paper, large print books and magazines, large print checks and many other useful devices help with coping with vision loss.

In addition, individuals may need to work with an occupational therapist to learn to use these devices effectively. A social worker can to identify community based programs that may be beneficial. Most people who have had expert Low Vision Rehabilitation can learn to read, write, use their computer and generally function at a relatively high level.

However, Low Vision Rehabilitation in no way affects the physical condition of the eye. It cannot make the disease better and it cannot make it worse. The goal of Low Vision Rehabilitation is to learn to use the remaining healthy vision as effectively and efficiently as possible.

A number of devices exist in the prior art for helping individuals cope with Macular Degeneration and other visual impairments. For example, U.S. Pat. No. 5,151,722 to Massof et al, incorporated by reference herein, discloses a head-mounted display for providing a monocular or binocular wide field of view. This display contains folding optics and a CRT for projecting a viewed image onto the eye. This and similar systems known as LVES (Low Vision Enhancement Systems), have a number of significant disadvantages. These systems are large, heavy and cumbersome and cannot be worn comfortably by the patient.

Because of their weight and awkward configuration, LVES systems also have the significant disadvantage that it is difficult for the patient to read effectively while wearing the unit and it is extremely difficult to move from place to place. This is because even very small amounts of movement will create image flutter and a blurring of the image that is projected onto the patient's eyes. This undesired motion and blurring of images causes the eyes to fatigue quickly and greatly increases eye strain.

These systems also cannot be used with a patient's normal prescription glasses because of their size and configuration, and the optics contained therein. Nor can they be readily optimized for changes in a patient's condition or even for different patients. Each unit must be customized for a particular condition and for a particular patient.

U.S. Pat. Nos. 5,125,046, 5,267,331, and 5,359,675, all of which are incorporated by reference herein, also disclose an image enhancement system for the visually impaired. This system is usable as a table-mounted display system or as head-mounted video spectacles. However, this system, like the LVES system, suffers from a number of significant disadvantages. These systems are also limited in that they cannot be easily reconfigured for the changing needs of the patient, and do not allow for the patient to wear his or her own prescription glasses while wearing the head-mounted enhancement system. This is a significant disadvantage in that the rehabilitation specialist cannot easily work with the patient while wearing the device to test and help improve the patient's vision. These systems also cannot be readily optimized for the needs of a different patient, but are instead designed and built for a specific application.

Because of these significant disadvantages inherent in conventional vision enhancement systems, a visual rehabilitation system is needed which significantly reduces the susceptibility of the system to motion, is easily adaptable to the changing needs of the patient, which can be readily optimized for the needs of different patients, and which will be a tremendous aid in the rehabilitation of patients coping with low vision and other visual impairments.

OBJECTS OF THE INVENTION

It is, therefore, an object of the present invention to provide a low vision rehabilitation system for aiding in the correction of vision of the visually impaired which can be specifically configured for the changing needs of a particular patient.

It's another object of the invention is to provide a low vision rehabilitation system which can be easily controlled by the patient and which is not cumbersome for the patient to wear.

It is a further object of the invention to provide a vision rehabilitation system which can be used in conjunction with the patient's normal prescription eyewear and which improves the testing and rehabilitation of the patient's vision when working with a rehabilitation specialist.

Another object of the invention is to provide a vision rehabilitation system having automatic, patient-controllable, scanning of images, such as text, to significantly reduce eye fatigue and enhance vision rehabilitation.

Yet another object of the invention is to provide a vision rehabilitation system which is adequately stabilized against undesired vibration and motion.

Other objects of the present invention will become apparent to those of ordinary skill in the art based upon the disclosure of the invention contained herein and in the appended claims.

SUMMARY OF THE INVENTION

The present invention is a head-mounted vision rehabilitation system for aiding in the rehabilitation of the visually impaired. The system of the present invention includes a headset, having an anterior portion extending over a patient's eyes, and a posterior portion partially encircling the patient's head. The anterior portion of the headset contains a spacing means to allow the headset to be worn with the patient's prescription eyeglasses. The present invention also includes a camera for imaging an image source located at a distance from said camera. The camera includes a focusing means, such as a static lens or adjustable "zoom" lens configuration, or even an auto-focusing lens configuration, which focuses light from the image source onto an electro-optical sensor to create an image signal based upon the light from the image source.

The present invention further includes a disengageable connector for connecting the camera to the anterior portion of the headset. The disengageable connector may include a "hot shoe" to allow electrical signals to communicate between the camera and the headset. The disengageable connector allows for the camera to be easily removed from the headset and replaced with a different camera.

A coherent video display is included, which is located within the anterior portion of the headset and receives the image signal from the camera to recreate the image onto the patient's eyes. A control unit, which is in communication with the camera and the video display, controls the operation of the vision rehabilitation system.

In accordance with another embodiment of the present invention, a multilens/multi-camera system is used to allow the patient to select between discrete levels of magnification depending upon the patient's condition and the image to be viewed. This multi-lens system may also be used with a positive/negative image invertor to create an inverse image on the patient's eyes.

In yet another embodiment of the present invention, a scanning system is included to allow the patient to scan an image, such as text, without movement of the patient's head or the headset. This scanning mechanism may incorporate mechanical movement of the camera, or movement of the electro-optical sensor or focusing system in relation to each other. Alternatively, the scanning mechanism may incorporate an oversized electro-optical sensor and image-processing electronics to electronically scan the incident image across the face of the oversized electro-optical sensor.

In a still further embodiment of the invention, a stabilization system is used to reduce the amount of image flutter from undesired vibrations and to reduce blurring of the detected image by the electro-optical sensor. The stabilization system may include the use of motion sensors, such as inertial sensors or the like, an optical wedge and a mechanical actuator or driving motor for moving the optical wedge. Alternatively, the stabilization system may incorporate an oversized electro-optical sensor and processing electronics which compensate for any undesired movement of the image across the face of the oversized sensor.

DETAILED DESCRIPTION OF THE PREFERRED EMBODIMENT

The invention will be understood more fully from the detailed description given below and from the accompanying drawings of preferred embodiments of the invention, which, however, should not be taken to limit the invention to a specific embodiment but are for explanation and understanding only.

Figure 1:
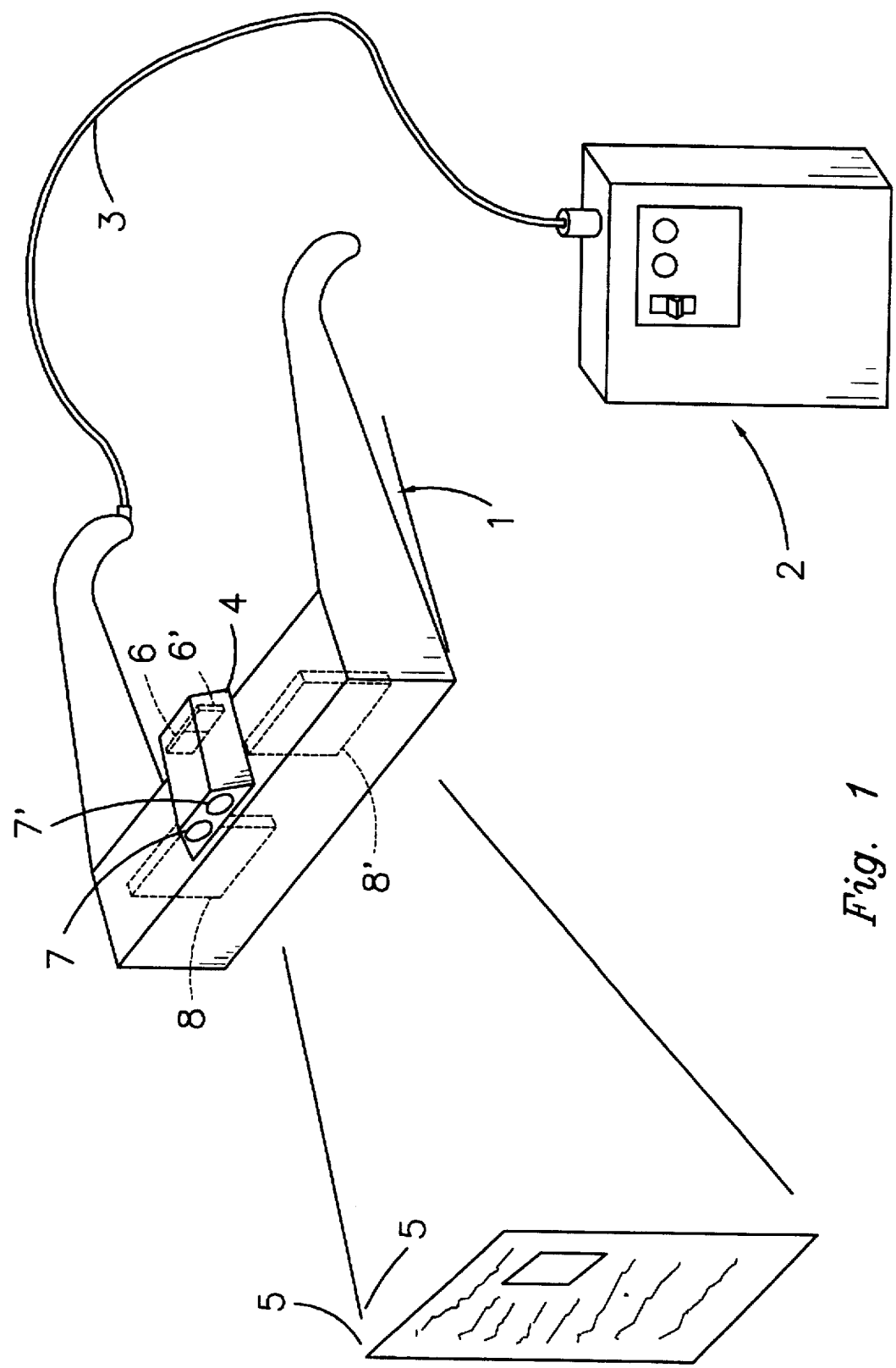
FIG. 1 is a drawing of a preferred embodiment of the invention to be worn by the patient.

As shown in FIG. 1, the present invention generally includes headset 1, containing the imaging components described in more detail below, and control unit 2, which is connected to headset 1 by communication cable 3. Control unit 2 includes control electronics, for controlling various functional aspects of headset 1 through communication cable 3. Of course, a number of suitable means of transmitting appropriate control signals between control unit 2 and headset 1 may be used, such as standard wire, coaxial cable, fiberoptic cable, and even radio or infrared transmission without the need for a connecting cable. Control unit 2 may also include a battery for powering the entire device, in a conventional manner. Alternatively, an outside power source, such as standard AC current, may be used, and headset 1 and control unit 2 may also be powered separately.

Headset 1 includes video camera module 4 positioned atop the anterior portion of headset 1 for generating an image signal based upon image source 5 located at a distance from the camera. The invention may include one or multiple cameras, depending on the patient's condition and the application for which the system is to be used. Camera module 4 preferably incorporates electro-optical sensors 6 and 6' which may be CCDs (Charge Couple Devices) or similar components, which can be produced very small in size and lightweight, while retaining a high resolution and light-gathering power.

Camera module 4 also preferably includes lenses 7 and 7' which are selected to provide the appropriate focal point for clear viewing of image source 5 and the proper magnification needed to correct the visual impairment of the patient. Lenses 7 and 7' may consist of single static lenses or an arrangement of lenses to provide "zoom" and autofocusing functions.

Headset 1 also by includes video displays 8 and 8' for displaying the image produced by camera module 4. Video displays 8 and 8' preferably include LCD (Liquid Crystal Display) panels which are compact and lightweight, and which provide a coherent image display to the patient's eyes. The coherent display of the LCD panels, coupled with the high resolution and light gathering power of the CCD cameras, provides the patient with a high contrast, highly magnified image, which can significantly aid in improving the patient's vision.

Figure 2C:
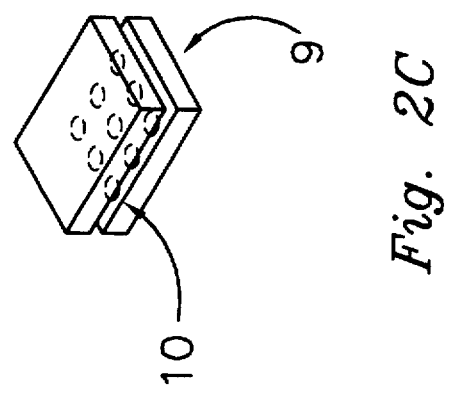
FIGS. 2(a), 2(b) and 2(c) are drawings of an embodiment of the invention incorporating a disengageable connector.
Figure 2B:
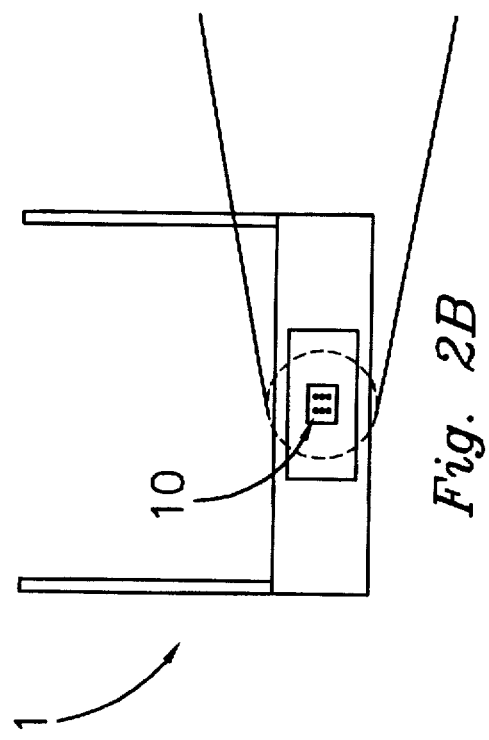
Figure 2A:
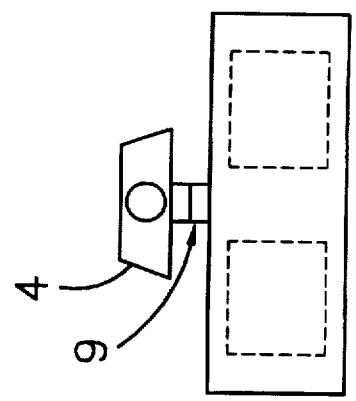

FIG. 2 discloses the use of disengageable connector 9 which allows for the interchangability of the system components. Disengageable connector 9 is mounted atop the anterior portion of headset 1 and may also contain contacts 10 to allow for the exchange of signals between camera module 4, video displays 8 and 8', and control unit 2 through communication cable 3. Disengageable connector 9 is preferably a "hot shoe" interface, containing electronic contact pads such as those present on conventional picture cameras, video cameras, and the like.

The use of a hot shoe allows attachment and removal of the camera module 4 from the headset via an easy to use, snap-on/snap-off interface. The patient simply activates a mechanical release to remove camera module 4. Likewise, the user engages a simple mechanical device to attach a new camera/lens module. The hot shoe interface includes multiple electrical (insulated) contacts to transfer electrical signals and power to and from the camera/lens module. These electrical power and signal contacts include the following possible functions, among others:

1. camera power
2. video signals
3. lens choice signal
4. auto-iris signal
5. autofocus signal
6. lens stabilizing electronic signal
7. lens or CCD sensor horizontal or vertical motion signals
8. zoom lens signal The ability to easily change the camera and/or lens system of the invention is a significant advantage over conventional systems since it has been discovered by the inventors that proper selection of the image magnification in conjunction with other corrective factors dependent on the patient's visual condition can dramatically improve the patient's ability to see and interpret images.

The invention also has the significant advantage in that it incorporates current miniaturized solid state video technology, such as the CCDs and the LCD panels described above, and has the significant advantage of allowing for the use of a large number of combination of lenses and cameras, both stationary and moving, which can be selected to configure the invention for the particular visual needs of the patient. A number of these combinations are described below, and are contained in the accompanying drawings. This interchangability of components is a significant advantage over conventional systems in that it allows the rehabilitation specialist and the patient to work together in achieving a system which is optimized for the needs of that particular patient. Conventional systems, such as the LVES system, do not have this interchangability. In particular, these systems cannot even be used in conjunction with the patient's normal prescription eyewear.

A number of embodiments of the camera module 4 can be employed to view image source 5. These include single/multiple monochrome video cameras, single/multiple color video cameras, single/multiple fixed focus lenses, zoom, autofocus, image-stabilized lenses, a stationary lens and video camera, and a moving video camera with respect to the lens and vice versa.

The number of possible combinations listed above is not exhaustive and illustrates the significant advantage of the invention in allowing the system to be specifically configured for the needs of the patient. The hot shoe concept of the present invention is particularly advantageous, since the ability to interchange the "front end" viewing optics, camera and scanning hardware while maintaining and keeping the remainder of the system intact is a significant benefit over conventional systems, such as LVES. This provides the significant advantages of ease of use by the patient, the ability to easily change the functions of the system during rehabilitation, and the ability to upgrade the system as new camera/lens modules become available.

The camera/lens arrangement on headset 1 is used to view a close scene (such as printed, graphic or photographic material), a person's face across a table, or something further distant. Image source 5 is detected by electro-optical sensors 6 and 6' through lenses 7 and 7' and is directed to video displays 8 and 8'. For example, if electro-optical sensors 6 and 6' are CCDs, incident light, which is focused through lenses 7 and 7' is converted by the light-sensitive material on a detecting area of the CCDs into an electrical signal representative of image source 5, which is carried in a conventional manner to the LCD panels of video displays 8 and 8'. The LCD panels then convert this electrical signal back into an optical image and coherently project that image onto the patient's eyes.

A significant advantage of the present invention is that the system can be used along with a patient's normal eyesight or prescription glasses. Unlike conventional systems, the present invention does not require that the video system be specifically tailored to the user's prescription. A person with normal eyesight can, of course, view the video display directly. A person with prescription glasses can easily put on or take off the headset of the present invention without removing their own glasses. Additionally, the headset can be made to pivot up and out of the way of the patient's eyes when not in use or when testing the patient's vision and configuring the system with the rehabilitation specialist.

Figure 3:
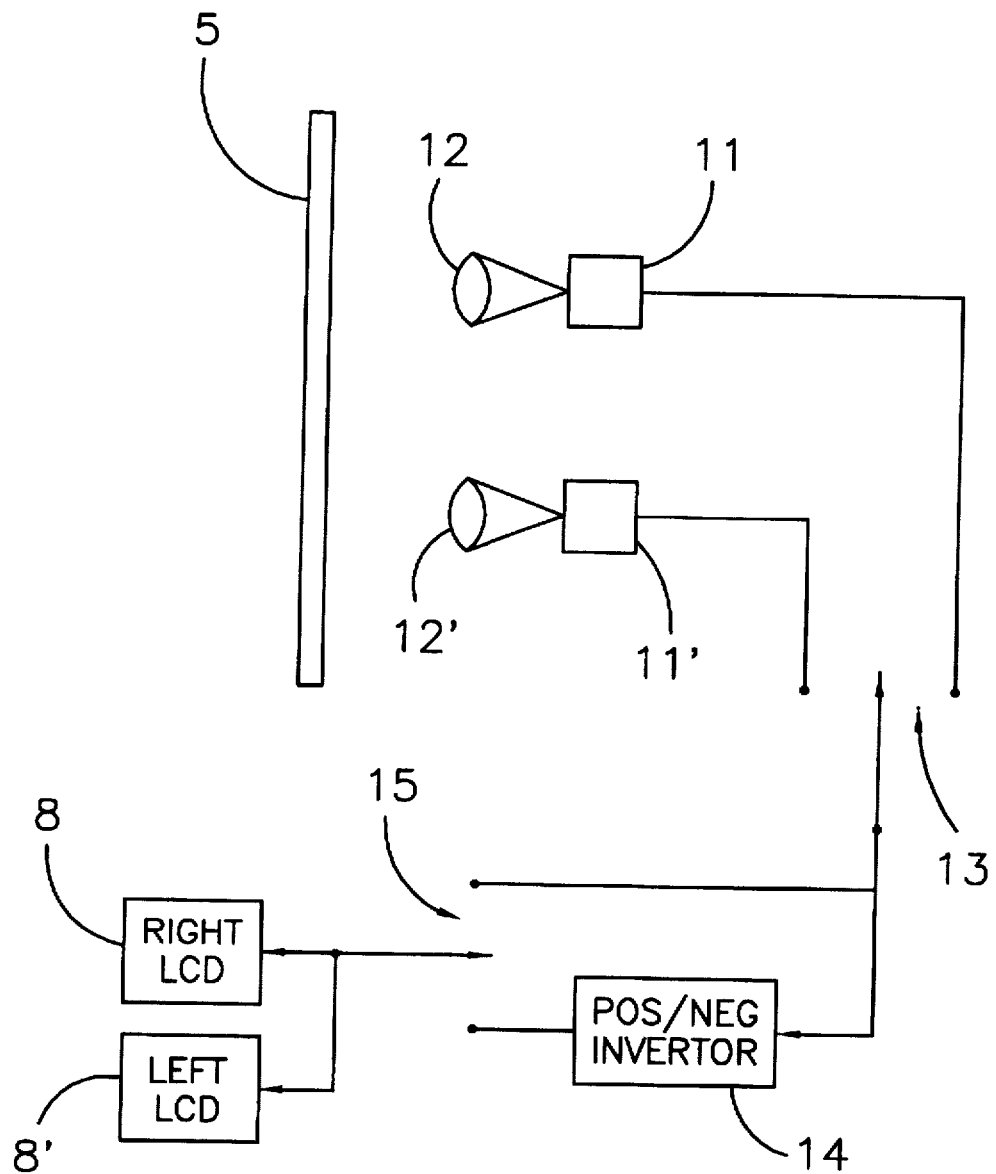
FIG. 3 is a drawing of an embodiment of the invention incorporating multiple lenses and electro-optical sensors.

FIG. 3 shows a block diagram of an embodiment of the invention for a two-camera system. CCD sensor 11 and lens 12 are used to view image source 5 close up, such as when viewing printed material, graphics, photographs or similar objects. A typical distance from lens 12 in this situation is 18 inches. CCD sensor 11' has lens 12' focused at a scene such as a face or other similar object which is positioned further away, for example, at 3–4 feet.

The two image signals from these cameras are transmitted to camera selection switch 13, which may be contained in control unit 2. The patient selects either camera 11 or 11' to display the scene from the corresponding camera onto LCD displays 8 and 8' in headset 1.

Before reaching the LCD displays, however, the chosen video signal can also be switched through a positive/negative electronic circuit 14, which may be in control unit 2, by switch 15 to convert the normal image signal to a negative one. This image inversion system has the significant advantage in that some objects are more discernible when displayed in video negative form, since some patients see objects, writing, etc. better in negative video.

Of course, multiple lenses and/or cameras can be used without the image invertor if necessary. Additionally, it is possible to use more than two cameras, selectable by the patient to provide different focal lengths and different magnifications of image source 5 on the LCD displays. For example, typical focal lengths for a two-lens system would have a focal length of lens 1 of 50–100 mm and a focal length of lens 2 of 25–50 mm. For a four-lens system, the focal lengths might be 50–100 mm, 25–50 mm, 25 mm, and 50 mm of the lenses respectively.

Figure 4A:
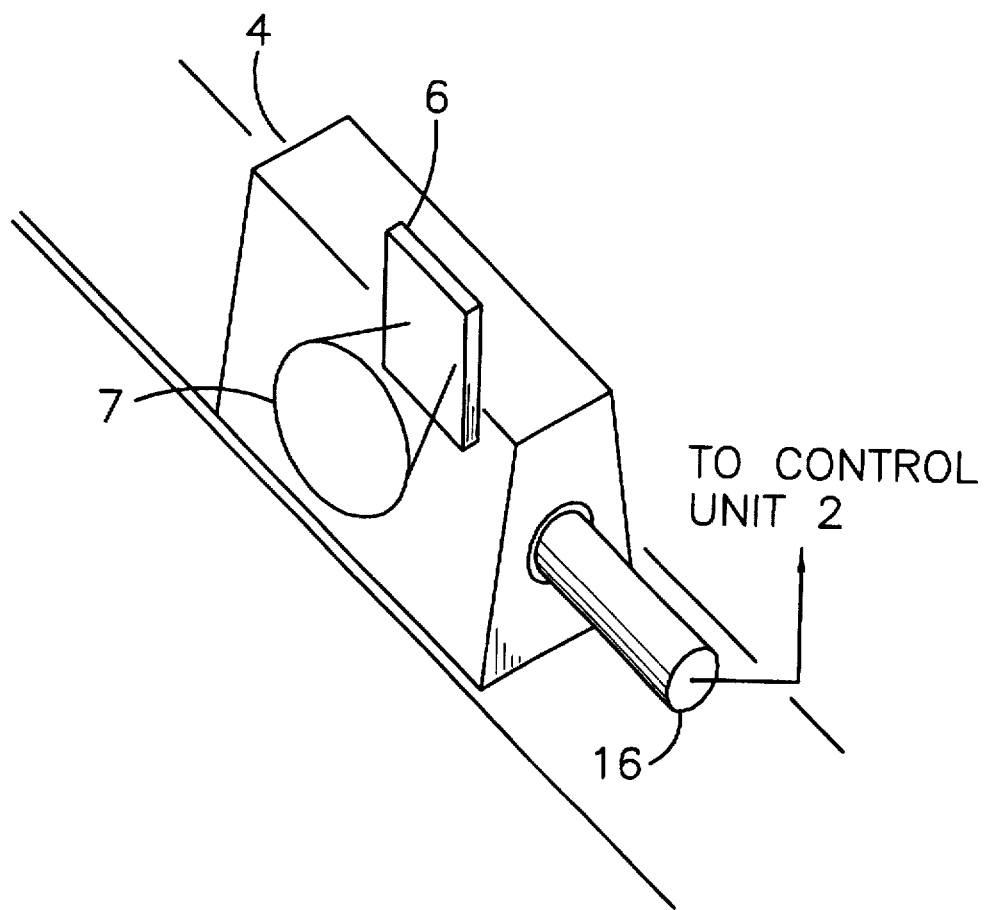
FIGS. 4(a), 4(b), and 4(c) are drawings of embodiments of a scanning system of the invention.

A mechanical or remote electromechanical device can be provided to move or rotate the camera module 4 in order to change the pointing direction of the system or to scan an image. An embodiment of this device is shown in FIG. 4(a). Motor 16 is used to rotate camera module 4 on headset 1 either vertically or horizontally. Of course, contacts 10 of disengageable connector 9 would, in this instance, be configured in a conventional manner to prevent interruption of signals to and from camera module 4 over the entire range of motion of the device. Motor 16 would be controlled by control unit 2 through communication cable 3 in a conventional manner.

Figure 4B:
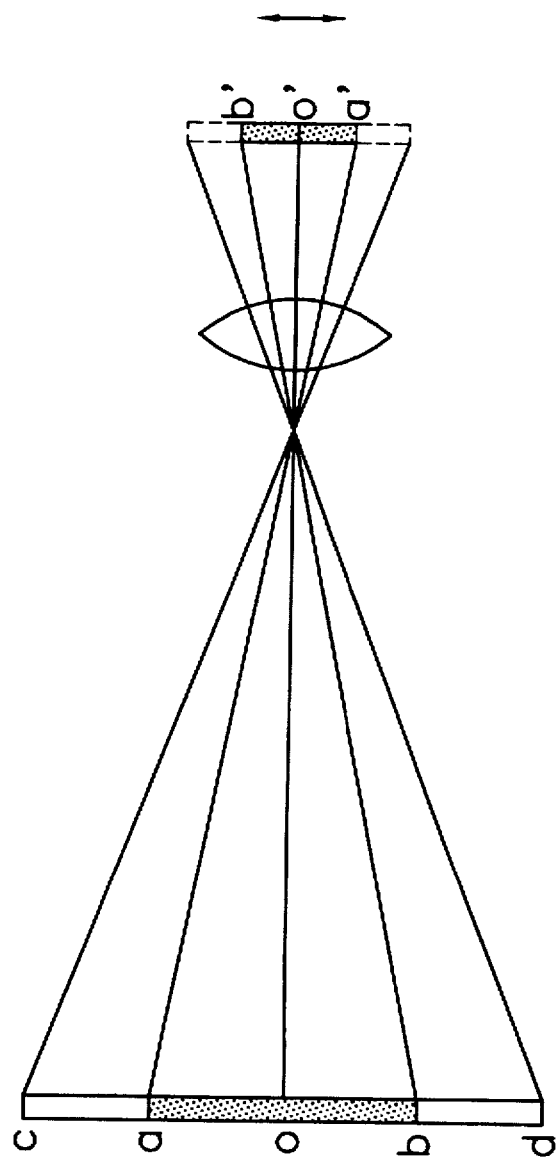

Another, particularly advantageous embodiment of the invention involves changing the pointing angle of the camera module 4 by moving only sensor 6 relative to lens 7. This is illustrated in FIG. 4(b) for changes in the horizontal direction. FIG. 4(b) shows lens 7 and sensor 6 horizontally viewing image source 5 of extent a, o, b, as determined by the focal length of lens 7, the horizontal width of sensor 6, and the distance from the lens to image source 5. By utilizing motor 16 to move sensor 6 only (or in the alternative lens 7) in the horizontal direction a distance of o'b' (or o'a') the image oc (or od) can be scanned onto sensor 6.

If the sensor of sensor 6 is moved linearly from o' to b', image source 5 is scanned linearly from o to b. Of course, image source 5 can be similarly scanned in the opposite direction to encompass c and d as part of the image displayed in the LCD display. Since the size of the sensor is small (typically in the range of 3–5 mm), the movement of sensor 6 is easily accomplished inside camera module 4. Instead of motor 16, a linear actuator or other similar device well known in the art can be used.

By scanning image source 5 in the manner of the invention, a change in horizontal (or vertical) pointing of the system can be achieved without requiring horizontal (or vertical) motion of headset 1 itself. This provides the significant advantage that, when reading a page of printed text, the relative horizontal motion of the lens and CCD sensor causes the viewer to "read" the text from left to right across a page and then down a page while the patient can remain stationary—thus reducing undesired vibration of the image and eye fatigue.

Figure 4C:
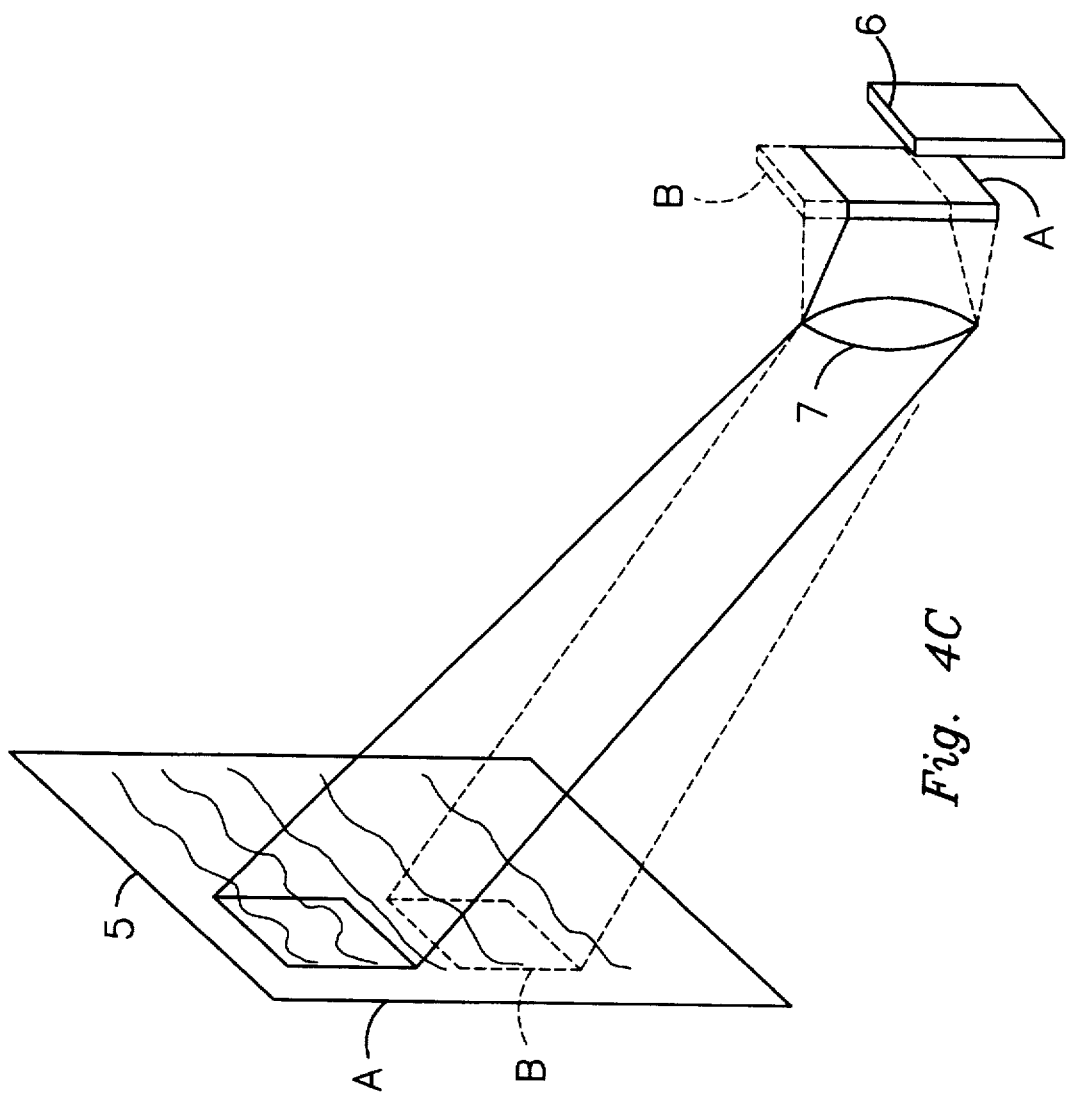

This implementation of the invention is demonstrated in FIG. 4(c). As shown in FIG. 4(c), when the top of image source 5 is being viewed (indicated by designation "A"), the sensor is at location A'. When sensor 6 is moved up to position B', the lens/camera pointing direction corresponds to the center of the page designated as "B". By combining this vertical movement with the horizontal scanning previously described, reading of the entire page can be easily accomplished in small or large steps, as controlled by the patient, or automatically via a program incorporated into the electronics of control unit 2. Such control programs may be incorporated into a programmable microprocessor or other integrated circuit. A detailed description of electronic scanning can be found in U.S. Pat. No. 4,963,962 to Kruegle et al, the disclosure of which is incorporated by reference herein.

The scanning mechanism of the invention can be combined with the multiple fixed lens aspect of the invention to provide yet another significantly improved technique for aiding the visually impaired. For example, a single CCD sensor can be rotated to switch between multiple lenses. This conserves CCD sensor usage.

Multiple lenses can be used with one CCD camera producing multiple magnification. To accomplish horizontal scanning or change of lenses (and the resultant scene viewed by the patient) the single CCD sensor is moved in the focal plane of the lens or moved from one lens' focal plane to the next lens' focal plane. This technique allows for multiple magnification and also scene scanning—horizontally or vertically—with one CCD sensor. Mechanical motion between the CCD sensor and the lens is accomplished with a suitable motor or linear actuator.

Typical distances for this movement are 2–4 mm. The 2–4 mm moved by the CCD sensor corresponds to several inches moved at the scene location. As an example, at 18 inches from the lens, a 3 mm (0.12 inch) horizontal CCD movement produces a 2.16 inch horizontal movement when using a 1 inch focal length lens according to the following equation:

$$H = 18 \text{ inches}/1 \text{ inch} \times 0.12 \text{ inch} = 2.16 \text{ inches}$$

At 36 inches from the lens, a 50 mm focal length lens produces a horizontal movement with the same 0.12 inch movement of the CCD according to the following equation:

$$H = 36 \text{ inches}/2 \text{ inches} \times 0.12 \text{ inches} = 2.16 \text{ inches}$$

Figure 5A:
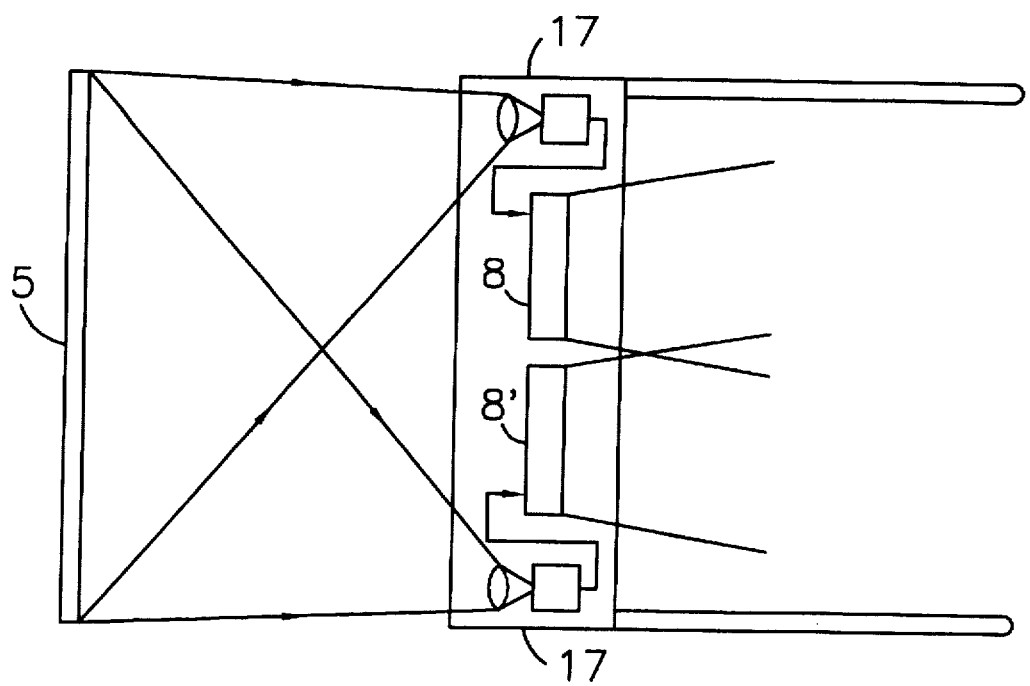
FIGS. 5(a) and 5(b) are drawings of an embodiment of the invention incorporating a binocular imaging system.
Figure 5B:
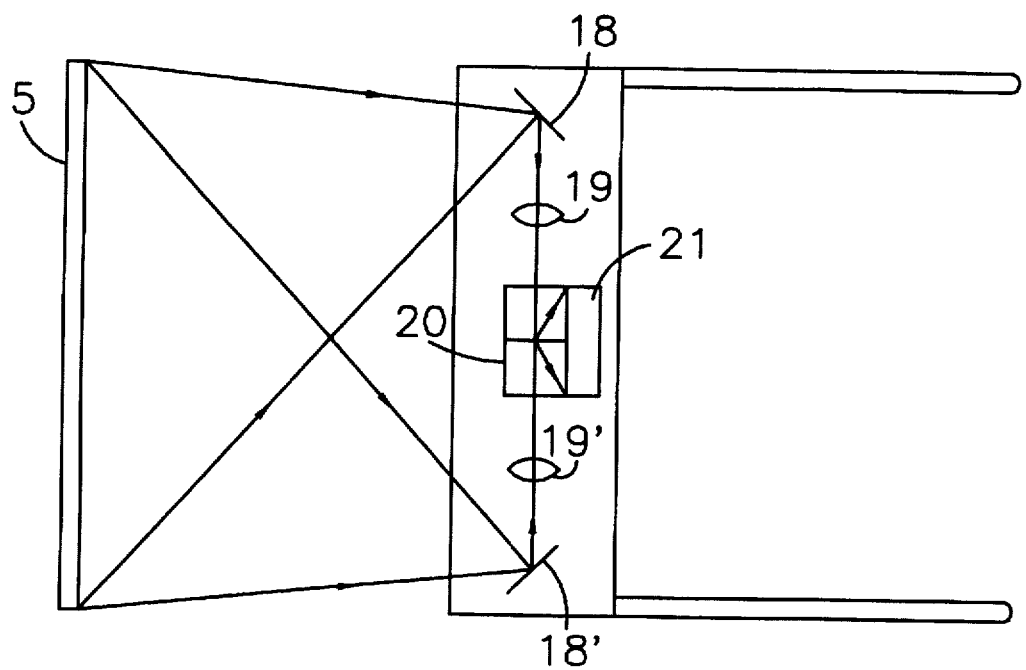

The present invention can also produce binocular or "stereo" vision through the use of either two CCD sensors and two lenses, or one sensor, and the ingenious use of two lenses and an optical splitter/combiner. FIGS. 5(a) and 5(b) illustrate these two embodiments of the invention. FIG. 5(a) shows the use of two CCD cameras, while FIG. 5(b) shows an optical splitter/combiner embodiment of the present invention.

In FIG. 5(a), right eye lens/camera 17 sends an image signal to right eye LCD display 8 and left eye lens/camera 17' sends an image signal to left eye LCD display 8'. In FIG. 5(b), image source 5 is displayed in 3-D via the use of mirrors 18 and 18', lenses 19 and 19', optical combiner 20, and CCD sensor 21. Optical combiner 20, which can be a prism, mirror or similar device, transfers the right eye image onto the right half of the CCD sensor 21 and the left eye image onto the left half of the sensor. To display the two-part image onto to the patient's eyes, the image from the left half of the sensor is processed, either by electronics present in control unit 2 or additional electronics located in camera module 4, and transmitted to the left LCD; and the image from the right half of the sensor is similarly processed and transmitted to the right LCD panel. The incorporation of stereo vision into the invention provides the significant advantage of allowing the patient to experience proper depth perception—important for viewing three-dimensional objects such as faces and the like.

By moving the two camera/lens pairs in FIG. 5(a) closer together or farther apart, the "stereo" effect changes. Likewise, in FIG. 5(b), moving the mirrors closer together or farther apart changes the stereo effect (closer equals weaker, farther equals stronger).

Another advantageous feature of the invention is the use of a zoom lens to produce variable fields of view and variable magnification and the use of an autofocusing mechanism. For convenience of the patient, the zoom lens controls are preferably located in control unit 2 and allow the patient to adjust the zoom lens as needed. The ability to modify the magnifying capability of the video enhancement system, whether continuously (as with a "zoom" lens) or discretely (as with multiple lens) is an important advantage of the present invention, particularly with patients having to cope with Macular Degeneration.

In patients experiencing Macular Degeneration, portions of the retina of the eye are no longer capable of responding properly to incident light, causing the creation of a "blindspot" in the patient's vision. As the retina deteriorates, this blindspot increases in size and encompasses a greater part of the patient's visual field. As a result, patients are often limited only to the peripheral field of vision.

By being able to change the magnification of the image being viewed, the patient is now able to effectively change the size of the blindspot in relation to the information present in the visual field. Patients using the system of the present invention can effectively see as if no such blindspot existed. To "eliminate" the blindspot, the patient can adjust the magnification to the point at which only the peripheral vision is used and the blindspot seems to disappear.

Figure 6A:
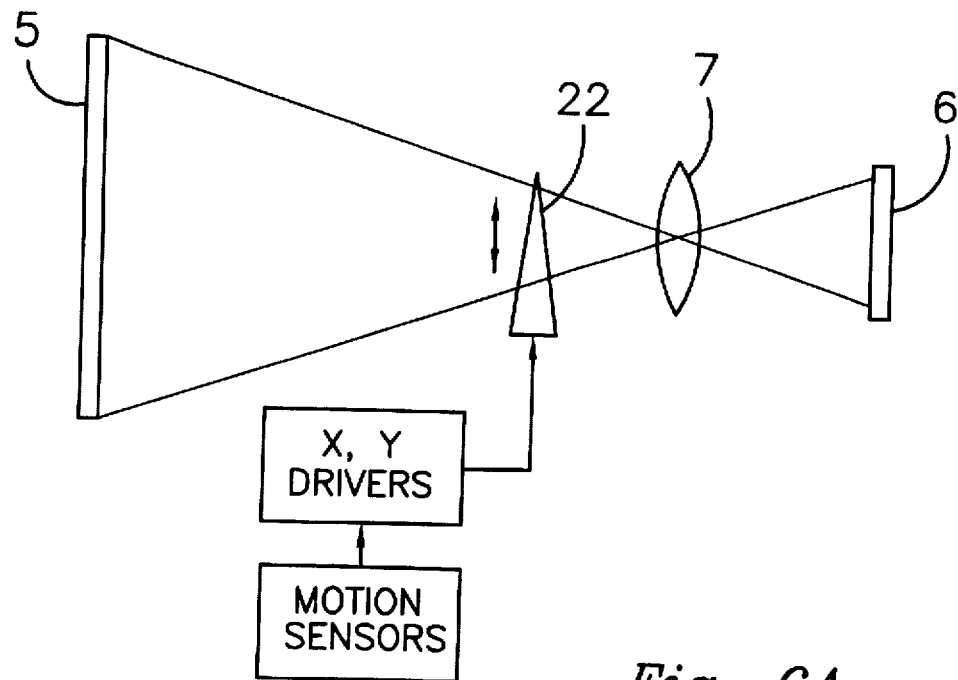
FIGS. 6(a) and 6(b) are drawings of an embodiment of a stabilization system of the invention.
Figure 6B:
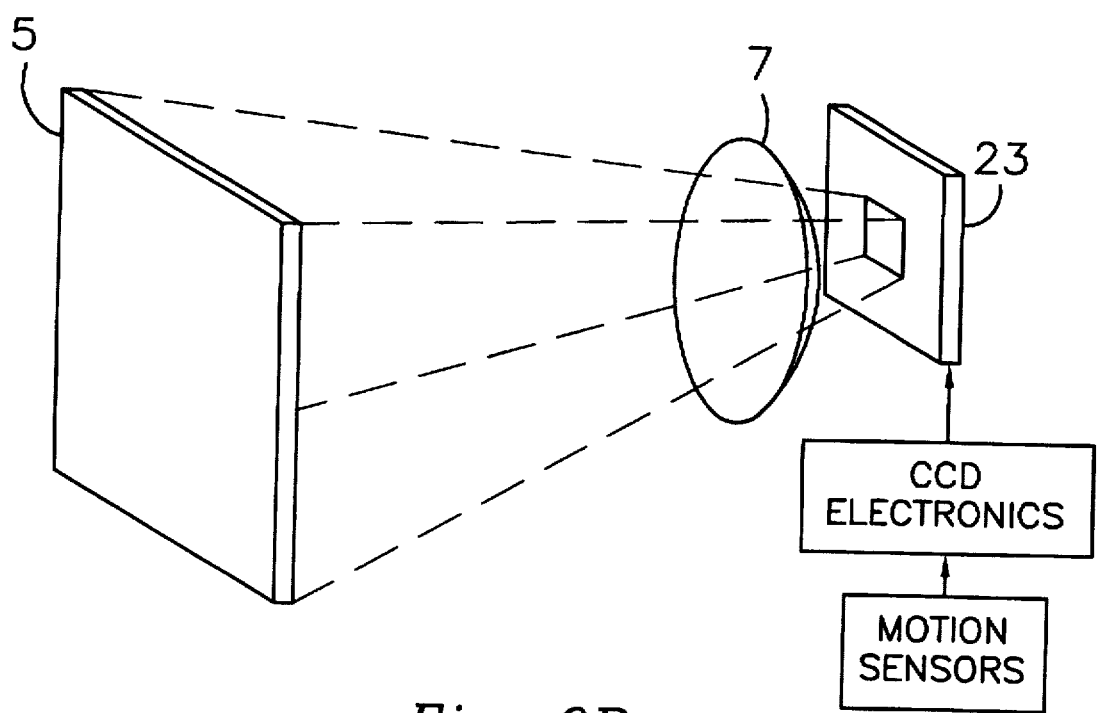

Because of the degree of magnification of the images being viewed by the patient, visual enhancement systems are highly sensitive to motion. The greater the magnification, the greater the amount of image vibration and blurring from the smallest amount of motion. This greatly increases eye fatigue and strain on the patient. Accordingly, it is another advantageous feature of the invention to incorporate and stabilize the optical system, which removes external vibrations and significantly reduces any blurring or deforming of the image scene on the CCD sensor. Stabilization of the system can be achieved both optically and electronically. FIGS. 6(a) and 6(b) illustrate the stabilization techniques of the invention.

The optically stabilized lens shown in FIG. 6(a) works by sensing X, Y (vertical and horizontal) motion, acceleration, etc. and correcting for the image motion on the sensor by changing the optical power of optical wedge 22, which is located in front of the lens of camera module 4, in the X and Y directions. Motion in the X or Y direction can be detected by using conventional motion sensors, well known in the art, such as inertial sensors or the like. Movement of optical wedge 22 can be accomplished through the use of a motor, actuator, or similar device.

The electronically stabilized lens shown in FIG. 6(b) operates by focusing the scene image on an oversized CCD sensor 23 and electronically moving the scene image (on the oversized part of the sensor) to compensate for the unwanted X, Y vibration and motion of camera module 4. For example, conventional motion sensors and actuators can be used to constantly reposition oversized CCD sensor 23 to maintain the entire image within the surface of the sensor. The image signal produced by oversized CCD sensor 23 thus remains unchanged even though the image itself may move across the face of the sensor. Since the video signal remains unchanged, the image displayed on the LCD panel also remains stable.

Alternatively, an image processor can be incorporated into control unit 2 (or in headset 1) to electronically compensate for changes in the position of the image on CCD sensor 20. Such image processors are well known in the art.

These stabilization techniques can be used in conjunction with the scanning mechanism described above to maintain a sharp image on the LCD displays while an image is being scanned. This significantly reduces the patient's eye fatigue and significantly increases their ability to read printed text.

Figure 7:
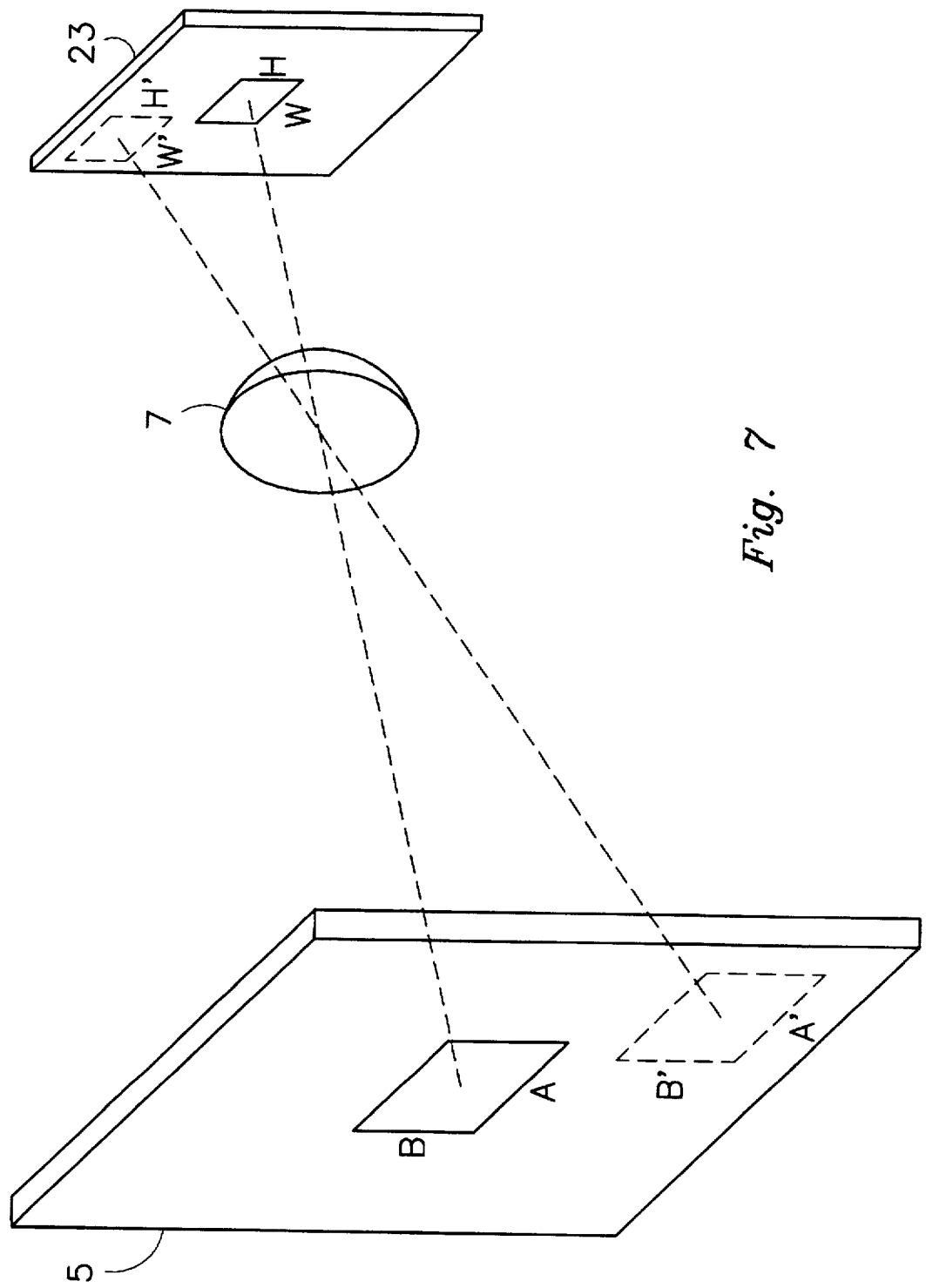
FIG. 7 illustrates the geometry of using an oversized image sensor for image stabilization and scanning in accordance with the invention.

FIG. 7 illustrates the geometry of combining electronic zooming, image stabilization and scanning in the present invention in the embodiment incorporating an oversized CCD sensor and appropriate electronics. In this configuration, the instantaneous electronic field of view, i.e., the view of image source 5 to be displayed on LCD displays 8 and 8' is substantially smaller than the full area of oversized CCD sensor 23.

Under normal, on-axis, one to one electronic zoom magnification, the LCD displays the scene image corresponding to A×B and W×H. If an off-axis scene at location A'×B' is to be viewed, the processing electronics display the scene image W'×H' on the LCD display. This corresponds to a camera/lens pointing shift from on-axis (A×B) to off-axis (A'×B'), accomplished by jumping from the on-axis pointing direction to the off-axis pointing direction. To accomplish horizontal (or vertical) scanning, the electronics simply moves the incident image linearly across the surface of oversized CCD sensor 23 from on-axis pointing to off-axis pointing.

Although the present invention has been described with reference to particular embodiments thereof, it will be appreciated that many variations may be resorted to without departing from the spirit and scope of the invention as set forth in the appended claims. For example, a variety of control electronics including integrated circuit technology and microcontrollers may be used. Controllable aspects of the invention may be incorporated into the headset itself. Additionally, various mechanical actuators and electro-optical sensing devices may be substituted for the motor controllers and CCD sensors described herein without departing from the scope of the invention.

What is claimed is:

1. A head-mounted vision rehabilitation system for aiding in the rehabilitation of a visually impaired individual comprising:

a headset, said headset having an anterior portion extending over said individual's eyes and a posterior portion partially encircling said individual's head, said anterior portion of said headset having a spacing means to allow said headset to be worn in conjunction with other eyewear;

a camera for imaging an image source located at a distance from said camera, said camera comprising a focusing means and an electro-optical sensor, wherein said focusing means focuses incident light from said image source onto said electro-optical sensor, said sensor creating an image signal based upon said incident light;

a coherent video display, located within said anterior portion of said headset for receiving said image signal from said camera and recreating said image from said image source onto said individual's eyes;

a disengageable connector for removably attaching said camera to said anterior portion of said headset;

a control unit, in communication with said camera, said video display and said headset, for controlling the operation of said head-mounted vision rehabilitation system.

2. The vision rehabilitation system of claim 1 wherein said disengageable connector further comprises a disengagedly communication means for communicating electrical signals between said camera and said headset.

3. The vision rehabilitation system of claim 1 wherein said electro-optical image sensor is a charged coupled device.

4. The vision rehabilitation system of claim 1 wherein said focusing means is an autofocusing lens system.

5. The vision rehabilitation system of claim 1 wherein said focusing means is a zoom lens system.

6. The vision rehabilitation system of claim 1 wherein said focusing means comprises a plurality of lenses, each of said lenses having a different level of magnification, and further comprising an actuator for moving any of said lenses and said electrical-optical sensor in relation to each other; and an actuator control means for controlling the operation of said actuator.

7. The vision rehabilitation system of claim 1 further comprising a scanning means attached to said camera to allow said camera to scan said image source without movement of said headset.

8. The vision rehabilitation system of claim 7 wherein said scanning means comprises:

an actuator for effecting movement of said electro-optical sensor relative to said focusing system; and an actuator control means for controlling movement of said actuator.

9. The vision rehabilitation system of claim 1 further comprising a stabilization means, connected to said camera, for stabilizing the image created on said electro-optical sensor by said incident light from said image source.

10. The vision rehabilitation system of claim 8 wherein said stabilization means comprises:

an optical wedge;

an actuator connected to said optical wedge for effecting movement of said optical wedge;

at least one motion sensor for detecting movement of said camera relative to said image source; and an actuator control means in communication with said actuator and said motion sensor for controlling movement of said optical wedge based upon said motion detected by said motion sensor.

11. The vision rehabilitation system of claim 8 wherein said stabilization means comprises:

an electro-optical sensor, said electro-optical sensor having an image-detection area greater than the image created by said incident light from said image source;

at least one motion sensor for detecting motion of said camera relative to said image source; and an image processing means for processing said image signal from said electro-optical sensor to stabilize said image recreated by said video display.

12. The video rehabilitation system of claim 1 wherein said electro-optical sensor has an image-detection area greater than the image created by said light from said image source and wherein said vision rehabilitation system further comprises:

at least one motion sensor for detecting motion of said camera relative to said image source; and an electronic control means in communication with said motion sensor, said electro-optical sensor, and said video display, said image control means being capable of electronically effecting movement of said image across said detection surface of said electro-optical sensor to controllably scan said image source and to stabilize said image recreated by said video display.

* * * * *